(12) United States Patent
Stegmann et al.

(10) Patent No.: US 10,588,963 B2
(45) Date of Patent: Mar. 17, 2020

(54) METHODS FOR PROVIDING ADJUVANTED VIROSOMES AND ADJUVANTED VIROSOMES OBTAINABLE THEREBY

(71) Applicant: Bestewil Holding B.V., Leiden (NL)

(72) Inventors: Antonius Johannes Henrikus Stegmann, Rijnsburg (NL); Joan Claudia Maureen Soei-Ken Tjon, Alphen aan den Rijn (NL)

(73) Assignee: BESTEWIL HOLDING B.V., Leiden (NL)

( * ) Notice: Subject to any disclaimer, the term of this patent is extended or adjusted under 35 U.S.C. 154(b) by 170 days.

(21) Appl. No.: 15/510,578

(22) PCT Filed: Sep. 12, 2014

(86) PCT No.: PCT/NL2014/050627
§ 371 (c)(1),
(2) Date: Mar. 10, 2017

(87) PCT Pub. No.: WO2016/039619
PCT Pub. Date: Mar. 17, 2016

(65) Prior Publication Data
US 2017/0189523 A1 Jul. 6, 2017

(51) Int. Cl.
| | | |
|---|---|---|
| *A61K 39/39* | (2006.01) | |
| *A61K 39/12* | (2006.01) | |
| *A61K 39/155* | (2006.01) | |
| *C12N 7/00* | (2006.01) | |
| *A61K 39/00* | (2006.01) | |

(52) U.S. Cl.
CPC ............ *A61K 39/39* (2013.01); *A61K 39/12* (2013.01); *A61K 39/155* (2013.01); *C12N 7/00* (2013.01); *A61K 2039/555* (2013.01); *A61K 2039/55572* (2013.01); *C12N 2760/18523* (2013.01); *C12N 2760/18534* (2013.01)

(58) Field of Classification Search
None
See application file for complete search history.

(56) References Cited

U.S. PATENT DOCUMENTS

| | | | |
|---|---|---|---|
| 7,329,807 B2 | 2/2008 | Vadrucci et al. | |
| 2009/0257950 A1* | 10/2009 | Sligar | C07K 14/47 424/1.69 |

FOREIGN PATENT DOCUMENTS

| | | | |
|---|---|---|---|
| WO | 0209746 A2 | 2/2002 | |
| WO | 2004045582 A1 | 6/2004 | |
| WO | 2004071492 A1 | 8/2004 | |
| WO | 2004110486 A1 | 12/2004 | |
| WO | WO2004/110486 | * | 12/2004 |
| WO | WO2004110486 | * | 12/2004 |
| WO | 2007099387 A1 | 9/2007 | |
| WO | 2013155448 A1 | 10/2013 | |
| WO | WO 2013/155448 | * | 10/2013 |
| WO | 2016039619 A1 | 3/2016 | |

OTHER PUBLICATIONS

Kamphuis et al., Influenza and other Resp Viruses 2013, vol. 7, pp. 1227-1236 (Year: 2013).*
Stegmann, Toon, et al. "Lipopeptide-adjuvanted respiratory syncytial virus virosomes: A safe and immunogenic non-replicating vaccine formulation." Vaccine 28.34 (2010): 5543-5550.
Schwaninger, Ruth, et al. "Virosomes as new carrier system for cancer vaccines." Cancer Immunology, Immunotherapy 53.11 (2004): 1005-1017.
Bungener, Laura, et al. "A virosomal immunization strategy against cervical cancer and pre-malignant cervical disease." Antiviral therapy 11.6 (2006): 717.
Bungener, Laura, et al. "Virosome-mediated delivery of protein antigens in vivo: efficient induction of class I MHC-restricted cytotoxic T lymphocyte activity." Vaccine 23.10 (2005): 1232-1241.
Kamphuis, Tobias, et al. "Immunogenicity and protective capacity of a virosomal respiratory syncytial virus vaccine adjuvanted with monophosphoryl lipid A in mice." PLoS One 7.5 (2012): e36812.
Committee for Medicinal Products for Human Use. "Guideline on adjuvants in vaccines for human use." Reproduction (2005).
Remington, Joseph Price, Arthur Osol, John T. Anderson, and John E. Hoover. "Remington's pharmaceutical sciences." (1975).
O'Flanagan et al., "Investigation of an Association Between Onset of Narcolepsy and Vaccination with Pandemic Influenza Vaccine, Ireland Apr. 2009-Dec. 2019", Euro. Surveill, vol. 19, No. 17, pp. 5-15; 2014.

(Continued)

*Primary Examiner* — Shanon A. Foley
*Assistant Examiner* — Myron G Hill
(74) *Attorney, Agent, or Firm* — Hoffmann & Baron, LLP

(57) ABSTRACT

The invention relates to the fields of immunology and vaccinology. Provided is a method for preparing adjuvanted virosomes, comprising the steps of: (i) providing an aqueous composition of non-adjuvanted virosomes comprising a membrane fusion protein; (ii) dissolving an amphiphilic adjuvant in a pharmaceutically acceptable non-aqueous solvent which can form a homogeneous mixture with water; and (iii) diluting said adjuvant solution in said aqueous virosome composition to induce insertion of adjuvant in the outer leaflet of the virosomal membrane while preserving membrane fusion activity of the virosomes. Also provided are adjuvanted virosomes obtainable by said method, and vaccines comprising the virosomes.

47 Claims, 8 Drawing Sheets

(56) References Cited

OTHER PUBLICATIONS

Figure 1A:
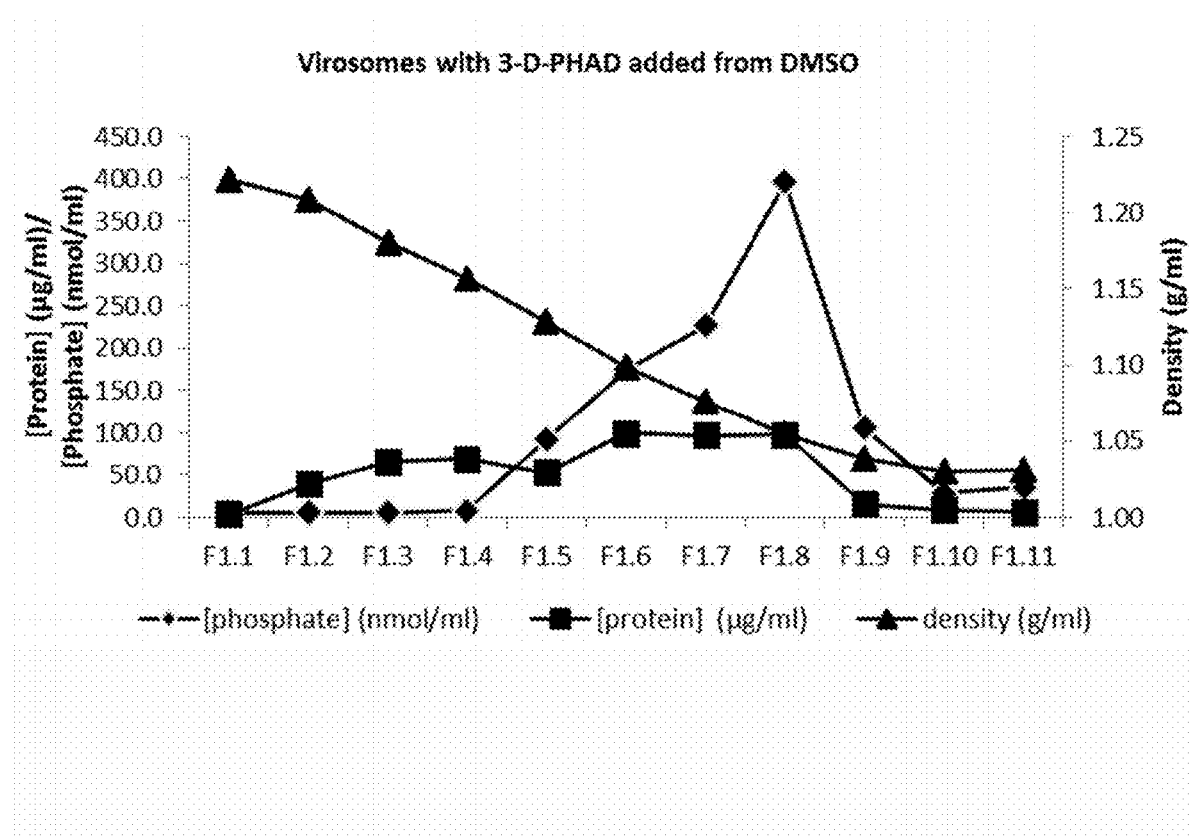

Bron et al., "Preparation, Properties, and Applications of Reconstituted Influenza Virus Envelopes (Virosomes)", Methods in Enzymology, vol. 220, pp. 313-331; 1993.
Lousada-Dietrich et al., "A Synthetic TLR4 Agonist Formulated in an Emulsion Enhances Humoral and Type 1 Cellular Immune Responses Against GMZ2—A Glurp—MSP3 Fusion Protein Malaria Vaccine Candidate", Vaccine, vol. 29, pp. 3284-3292; 2011.
Weijzen et al., "The Notch Ligand Jagged-1 is Able to Induce Maturation of Monocyte-Derived Human Dendritic Cells", The Journal of Immunology, vol. 169, pp. 4273-4278; 2002.
Struck, Douglas K., Dick Hoekstra, and Richard E. Pagano. "Use of resonance energy transfer to monitor membrane fusion." Biochemistry 2014 (1981): 4093-4099.

* cited by examiner

METHODS FOR PROVIDING ADJUVANTED VIROSOMES AND ADJUVANTED VIROSOMES OBTAINABLE THEREBY

This application is the U.S. National Phase of International Patent Application Number PCT/NL2014/050627 filed 12 Sep. 2014, of which is incorporated herein by reference.

The invention relates to the fields of immunology and vaccinology. Specifically, the invention relates to improved methods for providing virosomes, compositions comprising the virosomes and uses thereof. Vaccines against membrane-containing (enveloped) viruses mostly consist of killed or live attenuated viruses, or a preparation of their proteins (e.g. split virus vaccines or subunit preparations). Vaccination with killed viruses and protein preparations is safer than vaccination with replicating live attenuated or recombinant viruses, because the latter may mutate or revert back to wild-type virus. Subunit vaccines result in fewer local and systemic side effects and also have the clear advantage that they can be prepared from recombinant viral proteins expressed by cells rather than from virus, making production safer and eliminating the risk of contaminating vaccine preparations with live viruses. However, while the injection of live viruses generally induces strong cellular and antibody immune responses, protecting against future infections by the virus, non-replicating vaccines such as protein preparations, particularly membrane protein preparations, may fail to do so, inducing predominantly an antibody response. Infected cells can present material from the infecting pathogen on MHC-1 molecules on their surface, initiating a cellular immune response, such as a cytotoxic T-cell response. Many protein preparations that are not produced within the cell, will not be presented to the immune system in this manner. Live or killed viruses will also be taken up preferentially by specialized phagocytic cells of the immune system, such as dendritic cells, and be presented to other cells of the immune system, triggering an immune responses. These phagocytic cells patrol the body, ingesting particles of the size of viruses, but they do not efficiently take up purified proteins such as those from split virus or subunit vaccines. A particular problem with membrane proteins is that these are not soluble in water. Therefore, for successful presentation to antigen-presenting cells these proteins need some form of solubilization, allowing their use in a vaccine.

Numerous attempts to reinforce the immune response to subunit or protein preparations by physical or chemical means have been undertaken. The most important principle that emerges from these experiments is that multiple copies of the viral proteins need to be combined in particles that will be taken up efficiently by phagocytic cells. These particles can be virosome-like-particles, virosomes, Immune-Stimulating Complexes (ISCOMs), mixed micelles, proteosome preparations or proteins on microparticle carriers. Frequently, these particles also contain chemical substances (called adjuvants), that are meant to stimulate the immune system which address specific receptors on the phagocytes or the effector cells of the immune system.

Virosomes are a particularly useful kind of vaccine composition. Virosomes are the reconstituted membranes of enveloped viruses. They are generally produced by extraction of membrane proteins and lipids from enveloped viruses with a detergent or short-chain phospholipid, followed by removal of this detergent or short-chain phospholipid from the extracted lipids and viral membrane proteins, in fact reconstituting or reforming the characteristic lipid bilayers (envelopes) that surround the viral core or nucleocapsids (WO2004/071492, Stegmann T. et al., 1987, EMBO J. 6, 2651-2659). However, virosomes can be assembled basically from every integral membrane protein or peripheral membrane protein, or proteins conjugated to lipid anchors. An essential feature of virosomes is that they are particles of the size that is efficiently taken up by phagocytic cells of the immune system, and they closely mimic the composition, surface architecture and functional activities, particularly the membrane fusion activity, of the native viral envelope. Other molecules such as lipids, adjuvants or protein can be added to the solubilized membrane material. The membrane is then reformed by removal of the detergent or short-chain phospholipid, producing the virosomes. During membrane reformation, the added molecules will be included within the virosomes or integrated in the virosomal membrane. Virosomes can be used as vaccines or to deliver molecules into cells.

Influenza virus and Semliki Forest virus (SFV) are two classical examples of enveloped viruses. Enveloped viruses in general carry specific membrane proteins (the "spikes") which are required for binding to and entry of cells. These proteins are present on the surface of mature virions in a metastable conformation, known as the "pre-fusion form". After binding of the virus to the cells, the first step in infection of cells by these viruses is uptake of intact viral particles by receptor-mediated endocytosis. The endosomal compartment then becomes mildly acidic due to the activity of an ATP-dependent proton pump present in the membrane of the endosome. Triggered by these acidic conditions (pH 5-6), the viral spike proteins undergo a conformational change (from the "pre-fusion" to the "post-fusion" conformation) which drives fusion of the viral membrane with the membrane of the endosome. As a results of such a fusion the viral nucleocapsid and genetic material (DNA or RNA) enter the cytoplasm, and replication of the genome produces progeny virus.

Virosomes that are particularly active in inducing an immune response were found to have maintained the proper functions of the envelope proteins of the native virus, such as membrane fusion, receptor-binding and other activities. Preservation of receptor-binding and membrane fusion activity, indicating that the viral spike proteins on the virosomal membrane are in the pre-fusion form, is essential for the expression of full immunogenic properties of said virosomes. As a result of cytoplasmic delivery due to membrane fusion activity of the virosomes, MHC-1 exposition of epitopes from virosomal proteins has been demonstrated, resulting in the induction of protective cytotoxic T-cell activity (Bungener et al. Vaccine 23 (2005) 1232-1241, Bungener et al., Antiviral Therapy: 111 (6): 717-727). Therefore, virosomes with membrane fusion activity are useful as vaccines, having the safety profile of killed vaccines, while providing the immune systems with the stimulus representative of live vaccines.

It is known in the art to incorporate amphiphilic adjuvants in the membrane of virosomes to further improve the capacity of virosomal vaccine formulations to stimulate the immune response following injection or intranasal application of virosomes. See for instance WO2004/110486, wherein virus is solubilized with a detergent or short-chain phospholipid followed by viral nucleocapsid removal. Thereafter, the adjuvant dissolved in the same detergent or short-chain phospholipid, is added to the solubilized viral membranes to incorporate the adjuvant in the virosomes. The detergent or short-chain phospholipid is then removed, resulting in the formation of virosomes that include at least the viral membrane proteins and lipids and the adjuvants. Amphiphilic adjuvants incorporated into the virosomal membrane in this fashion have been shown to be stably integrated in the membrane (Stegmann, T et al. Vaccine 2010; 28(34): 5543-50; WO2004/110486) and enhance or alter the immune response following vaccination with these virosomes in preclinical trials (Kamphuis, T. et al. Plos One 2012; 7 (5):e36812).

However, the ratio between the protein and adjuvant concentration in the membrane is fixed at the formation of the virosomal membrane because they are both present in the same membrane. Also, although the adjuvant is incorporated into both leaflets of the membrane bilayer, only the adjuvant present in the outer leaflet is available to interact with the receptor present on the cells of the immune system.

The antigen/adjuvant ratio profoundly affects the immune response following vaccination. For example, for respiratory syncytial virus (RSV) virosomes containing a monophosphoryl lipid A adjuvant, is was found that a threshold concentration of the adjuvant was capable of skewing the immune response from a dominant Th2 response to a more balanced Th1/Th2 response (Kamphuis, T. et al. Plos One 2012; 7 (5):e36812).

In order to obtain marketing licensure for vaccines containing adjuvant (cf. "EMA guidelines on adjuvants in vaccines for human use": EMEA/CHMP/VEG/134716/2004), demonstration of adequate and consistent association of the antigen with the adjuvant is required, followed by a safety evaluation of the vaccine candidate in preclinical and then in clinical trials. The results of animal experiments are often not completely predictive of the effect of the vaccine in man. Particularly, the optimal antigen/adjuvant ratio is difficult to estimate. While a low adjuvant concentration is desired to minimize side effects, the adjuvant needs to enhance or alter the immune response in the desired fashion, and at high adjuvant concentrations other effects, such as tolerization or increased reactogenicity (i.e. the property of a vaccine of being able to produce common, "expected" adverse reactions, especially excessive immunological responses and associated signs and symptoms), are possible. Therefore, the optimal antigen/adjuvant ratio can only be determined by trial and error. Moreover, it is possible that for different groups of patients, such as elderly or infants, different ratios may be optimal. For vaccines formulated with a classical adjuvant, such as antigen absorbed to alum, antigen is produced under GMP (drug substance A), released for clinical trial, and it can then be mixed with GMP-grade alum (drug substance B) to form the drug product at the bedside, allowing easy testing of various adjuvant/antigen ratios. However, this approach is not possible for virosomes with incorporated amphiphilic adjuvant, since the ratio between antigen and adjuvant is already fixed at the reconstitution of the membrane.

Thus, the only way to test various adjuvant/antigen ratios using the currently available methods for preparing adjuvanted virosomes is to produce a large variety of virosomes with a different antigen/adjuvant combinations (each preparation constituting a drug substance), to perform the required preclinical safety and immunogenicity testing for each preparation, to release each preparation for clinical trial, and to test each of the different preparations separately. Clearly, this multiplies the costs of such trials by a very significant factor.

To overcome these problems, the present inventors sought to facilitate the clinical testing of adjuvanted virosomes. In particular, they aimed at minimizing the number of preparations requiring separate testing for preclinical safety, immunogenicity, release, clinical trial etc. A further goal was to minimize the amount of adjuvant used the while retaining immunogenicity.

It was observed that at least some of these goals could be met by adaptation of the conventional method for adjuvanted virosome preparation. More particularly, the novel method comprises preforming virosomes containing the antigen without adjuvant and by adding amphiphilic adjuvants dissolved in a suitable solvent. The dissolved adjuvant is mixed with an aqueous composition containing preformed virosomes, such that the adjuvant solvent mixes with the water, and the adjuvant integrates into the virosomal membrane. Thus, amphiphilic adjuvant are included in virosomal membranes after, rather than during virosome formation. This "two-step" method of the invention facilitates the formulation of virosome-based vaccines with different adjuvant/antigen ratios and forming virosomes with the adjuvant incorporated in the outer leaflet of the membrane only. Surprisingly, despite exposure of the (viral) proteins to the adjuvant solvent, the virosomes obtained according to this novel post-insertion protocol displayed fusion activities similar to the traditional incorporation method.

Accordingly, in one embodiment the invention provides a method for preparing adjuvanted virosomes, comprising the steps of:

(i) providing an aqueous composition of non-adjuvanted virosomes comprising a membrane fusion protein;

(ii) dissolving an amphiphilic adjuvant in a pharmaceutically acceptable non-aqueous solvent which can form a homogeneous mixture with water, and (iii) diluting said adjuvant solution in said aqueous virosome composition to induce insertion of adjuvant in the outer leaflet of the virosomal membrane while preserving membrane fusion activity of the virosomes.

The invention has important advantages for the preclinical and clinical testing of vaccines comprising adjuvanted virosomes. The pre-formed virosome composition will thus form "drug substance A", while the adjuvant in the solvent is "drug substance B". Only the safety and clinical testing for drug substance A and B is required. The combination of substance A and B into drug products with various adjuvant/antigen ratios can take place at the bedside.

Moreover, adjuvants have been known to produce various side effects, ranging from pain at the injection site to inflammations, to Bell's Palsy (Lewis, D. J H. et al., PLoSOne 2009 4(9):e6999) and narcolepsy (O Flanagan D. et al. PLoSOne 2014, 19(17)pii20789. Therefore, it is important to incorporate the lowest effective concentration of adjuvant. By integrating the adjuvant into the virosomal membrane during the conventional one-step process of forming the virosomal membrane, the adjuvant will be incorporated in both leaflets of the bilayer. However, only half the adjuvant, present in the outer leaflet of the membrane, can contact the cells of the immune system, thus the concentration that can contribute to unwanted side effects is twice the effective concentration. In contrast, in a method of the invention using pre-formed virosomal membranes, the adjuvant is inserted only in the outer leaflet of the membrane such that all of it will be available for interaction with the immune system. This allows for reducing the effective adjuvant concentration by half compared to conventional virosomes with adjuvant in both leaflets, thus potentially limiting side effects.

Post-insertion of amphiphilic adjuvant specifically into the outer leaflet of the virosomal bilayer has not been disclosed or suggested in the art. For example, whereas WO2007/099387 teaches that the immunostimulatory effect its virosome-like vesicles may be further increased by associating the vesicles with at least one adjuvant, it is only generally taught that the adjuvant may be encapsulated inside and/or incorporated in the lipid bilayer of, and/or freely combined with said vesicle. Nothing is mentioned or suggested about post-inserting adjuvant in the outer leaflet of the bilayer.

In a first aspect, the present invention provides a method for introducing amphiphilic adjuvants into the membrane of preformed virosomes. In a second aspect, the invention provides for virosomes with adjuvant present in the outer leaflet of the virosomal membrane only.

The term "virosome" refers to a liposome containing viral envelope proteins embedded in the lipid membrane. Virosomes are formed in vitro and do not contain viral core proteins. Generally, virosomes are spherical, unilamellar vesicles with a mean diameter of about 150 nm. In contrast to liposomes, virosomes generally contain functional viral envelope glycoproteins, such as influenza virus hemagglutinin (HA), neuraminidase (NA), or matrix protein 2 (M2), intercalated in the phospholipid bilayer membrane. To produce these virosomes, an aqueous suspension of ordinary virosomes without adjuvant can first be produced according to methods known in the art. Protocols of preparation are well-known by the skilled person in the art. Suitable protocols for the invention are described, for example, in WO 2004/045582 or EP 0 538 437. According to an embodiment, a virosome may be obtained either from a virosome vesicle as such, or from a vesicle resulting from the fusion of a virosome vesicle with a liposome vesicle.

The preparation of virosome vesicles may be made by any known method of the skilled person in the art such as described by Bron et al., Methods Enzymol. 220: 313-331 (1993). In one embodiment, the step of preparing virosomes involves the functional reconstitution of an enveloped virus, preferably a virus selected from the group consisting of Retroviridae; rubellavirus; paramyxoviridae; Flaviviridae; Herpesviridae; Bunyaviridae; Arenaviridae; Hantaviridae; Baculoviridae; Coronaviridae; Papovaviridae; Rhabdoviridae; Alphaviridae, Arteriviridae, Filoviridae and Poxviridae. Typically, functional reconstitution of an enveloped virus into virosomes comprises contacting an enveloped virus with a solution containing a short-chain phospholipid or a detergent allowing solubilisation of the viral envelope of said virus further comprising removing short-chain phospholipid or detergent from said solution allowing formation of a functionally reconstituted viral envelope. Preferably, the phospholipid or detergent is removed by dialysis, filtration, or absorption onto hydrophobic beads. Preferred hydrophobic beads include beads that are composed of polystyrene divinylbenzene. Useful lipids for preparing virosomes are short-chain phospholipid having a critical micelle concentration (cmc) of larger than 0.1 mM, preferably larger than 0.3 mM, more preferably larger than 1 mM. For example, very good results are obtained wherein the phospholipid is a phosphatidylcholine, preferably 1,2-diheptanoyl-sn-phosphatidylcholine or 1,2-dicaproyl-sn-phosphatidylcholine. See also WO2004/071492. Suitable detergents are also known in the art. Preferably, the detergent is a non-ionic detergent such as octa-ethylene-glycol mono (n-dodecyl) ether.

In a specific embodiment, virosome may be reconstituted from original viral membrane lipids and spike glycoproteins after solubilization of, for example, intact influenza virus with octaethyleneglycol mono(n-dodecyl)ether (C12E8), sedimentation of the nucleocapsid (the viral glycoproteins and lipids will remain in the supernatant), and removal of the detergent in the supernatant with a hydrophobic resin (Bio-Beads SM2) (Stegmann et al., Traffic 1:598-604, 1987). Preparation of virosomes containing HAs from different strains of viruses, may be performed with, equal amounts of proteins of those viruses solubilized with the non-ionic detergent octaethyleneglycol monododecyl ether.

After removal of the detergent with Bio-Beads SM2, virosomes-containing different types of fusion proteins may be formed. According to one embodiment, a virosome-like vesicle according to the invention may be obtained from a fusion of a virosome vesicle with a liposome vesicle.

Therefore, according to one embodiment, a virosome-like vesicle of the invention may comprise virosomal and liposomal lipids.

The virosomal membrane preferably comprises: (a) a lipid bilayer; (b) a membrane protein; and (c) optionally, further antigens. Preferably, the membrane protein is a viral membrane fusion protein. Preferably, the lipid bilayer has a lipid composition that is compatible with fusion, as induced by the fusion protein, of the viral membrane with a host cell of a natural host of the virus. Preferably the lipid composition is compatible with fusion at the optimal pH of fusion. It is possible to use any of a variety of enveloped viruses for the production of virosomes, such as there are, Retroviridae such as Human Immunodeficiency virus (HIV); rubellavirus; paramyxoviridae such as parainfluenza viruses, measles, mumps, respiratory syncytial virus, human metapneumovirus; flaviviridae such as yellow fever virus, dengue virus, Hepatitis C Virus (HCV), Japanese Encephalitis Virus (JEV), tick-borne encephalitis, St. Louis encephalitis or West Nile virus; Herpesviridae such as Herpes Simplex virus, cytomegalovirus, Epstein-Barr virus; Bunyaviridae; Arenaviridae; Hantaviridae such as Hantaan; Coronaviridae; Papovaviridae such as human Papillomavirus; Rhabdoviridae such as rabies virus. Coronaviridae such as human coronavirus; Alphaviridae, Arteriviridae, filoviridae such as Ebolavirus, Arenaviridae, poxviridae such as smallpox virus, or African Swine Fever virus, in the method as provided herein.

A fusion protein of a virus is herein understood to mean an integral membrane protein of a virus, usually an enveloped virus that, if expressed on the surface of a suitable cell, can induce fusion of the cell, at an appropriate pH, with cells that are a natural host for the virus. Examples of viral fusion proteins for incorporation into the reconstituted viral membrane include the Semliki Forest virus E1 protein, the Influenza virus hemagglutinin (HA) protein, the HIV gp120/gp41 proteins, the F proteins of paramyxoviruses. Also encompassed are (genetically modified) variants of a fusion protein which can mediate fusion with a target cell. Two types of fusion induced by viral fusion proteins can be distinguished. The first type of fusion, such as e.g. induced by the HIV gp120/gp41 proteins, or the paramyxovirus F proteins, occurs at neutral pH, usually at the surface of the targeted host cell. The second type of fusion, such as e.g. induced by the Influenza virus hemagglutinin (HA) protein, occurs upon internalization at lower pH (5.0-6.5) from within the endosomal compartment of the host cell. Both types of fusion are specifically included in the present invention.

The capability of the virosomes of the invention to fuse with a host cell is thus dependent on the presence of an appropriate viral fusion protein. However, this capability is further dependent of the lipid composition of the bilayer of the reconstituted viral membrane, as virosomes composed of certain synthetic lipids and viral fusion proteins have been described in the art that are incapable of fusion. The lipid composition of the virosomes is thus preferably chosen such that the membranes are capable of fusion with appropriate host cells at an appropriate pH. One preferred lipid composition that provides the virosomes with fusion activity is a lipid composition that comprises natural lipids of a virus. The term "natural lipids of a virus" is herein understood to mean those lipids that are present in the membrane of a virus grown on cells, preferably mammalian, insect or plant cells, or grown on embryonated eggs. The natural lipids of a virus are thus preferably obtained or isolated from virus particles thus grown, as opposed to synthetic lipids.

However, functionally reconstituted viral membranes of the invention may comprise purified lipids from other sources, e.g. purified or synthetic lipids, in addition to the viral lipids. The other lipids can be added to the virosome membranes during preparation. Fusion activity of the virosomes is generally optimally maintained when lipids similar to those of viral origin or lipid mixtures which closely resemble the lipid composition of the viral envelope are added. Thus, in line with the present invention a broad range of lipids can be comprised in said virosomal membrane. The group of lipids comprises neutral and charged phospholipids, steroid-derived lipids, neutral and charged synthetic lipids. A lipid composition for the provision of the virosomes with fusion activity is thus preferably a composition that is obtained or obtainable from natural viral membranes. Lipid compositions for use in the present invention thus include compositions exclusively composed of natural lipids of a virus, compositions composed of natural lipids of a virus supplemented with lipids from other sources, as well as compositions composed of lipids from various sources, which mimic the lipid composition of a natural viral membrane.

These lipids may comprise cholesterol and phospholipids such as phosphatidylcholine (PC), sphingomyelin (SPM), phosphatidylethanolamine (PE), and phosphatidylserine (PS). However, other phospholipids may also be added. These include, but are not limited to, phosphatidylglycerol (PG), phosphatidic acid (PA), cardiolipin (CL), and phosphatidylinositol (PI), with varying fatty acyl compositions and of natural and/or (semi) synthetic origin, and dicetyl phosphate. Ceramide and various glycolipids, such as cerebrosides or gangliosides, may also be added.

The virosome of the present invention preferably comprises lipids selected from the group consisting of cationic lipids, synthetic lipids, glycolipids, phospholipids, sterols, and derivatives thereof. Phospholipids preferably comprise phosphatidylcholine, sphingomyelin, phosphatidylethanolamine, phosphatidylserine, phosphatidylglycerol, phosphatidic acid, cardiolipin, and phosphatidylinositol with varying fatty acyl compositions. Cationic lipids are preferably selected from the group consisting of DOTMA (N-[(1-(2,3-dioleyloxy)propyl]-N,N,N-trimethylammonium chloride), DOTAP (N-[1-(2,3-dioleoyloxy)propyl]-N,N,N-trimethylammonium chloride, DODAC (N,N-clioleyl-N,N,-dimethylammonium chloride), DDAB (didodecyklimethylammonium bromide), TC-Chol (cholesteryl N-(trimethylammonioethyl)carbamate chloride), DC-Chol (cholesteryl N-(dimethylammonioethyl)carbamate chloride), or other cationic cholesterol derivatives, and stearylamine or other aliphatic amines, DPPE (dip almitoyl-phosphatidylethanolamines), DOGS (Dioleoyl-Glycero-Succinate), DOSPA (2,3-dioleoyloxy-N-[2(sperminecarboxamido)ethyl]-N,N-dimethyl-1-propanaminium trifluoroacetate), DOSPER (1,3-dioleoyloxy-2-(6-carboxyspermyl)propylamide), THDOB (N,N,N',N'-tetramethyl-N,N'-bis (2-hydroxyethyl)-2, 3,-dioleoyloxy-1,4-butanediammonium iodide), DOPA (Dioleoyl-sn-Glycero-Phosphate), DOTP (dioctyl tere-phthalate), DOSC (dioleoyl-succinyl-glycerol), DOTB (dioleoyl-e-(4'-trimethylammonio)-butanoyl-sn-glycerol), DOPC (Dioleoyl-sn-Glycero-Phosphatidylcholine), DOPE (Dioleoyl-sn-Glycero-Phosphatidylethanolamine) and the like. Especially preferred, the cationic lipid is chosen from cationic cholesterol derivatives such as TC-Chol (cholesteryl N-(trimethylammonioethyl) carbamate) or DC-Chol (cholesteryl N-(dimethylammonioethyl) carbamate). They may be formulated as small unilamellar liposomes in a mixture with PC (phosphatidylcholine). The virosomes of the present invention may preferably comprise egg-derived PC and, more preferably, DOPC (Dioleoyl-sn-Glycero-Phosphotidylcholine), DOPE (Dioleoyl-sn-Glycero-Phosphatidylethanolamine Examples of cholesterol or sterol derivatives that can be incorporated into virosomes of the invention include: cholesterol hemisuccinate, phytosterols such as lanosterol, ergosterol, and vitamin D and vitamin D related compounds.

To introduce the adjuvant into the outer leaflet of the preformed virosomes without adjuvant, the adjuvant is dissolved in a non-aqueous solvent that can be mixed with water. The solution is then added to the aqueous suspension of virosomes without adjuvant. Dilution of the solvent renders the adjuvant insoluble, and spontaneous integration into the virosomal membrane is accomplished.

The skilled person will be able to choose a pharmaceutically acceptable non-aqueous solvent capable of forming a homogeneous mixture with water, which can be described as a solution of only one phase. For example, it is selected from the group of solvents known in the art as "residual solvents in pharmaceuticals". These are defined as organic volatile chemicals that are used or produced in the manufacture of drug substances or excipients, or in the preparation of drug products. The expression "capable of forming a homogeneous mixture with water" is meant to indicate that, under the specific conditions used, the adjuvant solvent mixes with the aqueous phase of the virosomal composition to an extent that is sufficient to allow for contacting the adjuvant dissolved therein with the virosomes and induce insertion of adjuvant in the outer leaflet of the virosomal membrane. Suitable solvents dissolve the adjuvant efficiently and are water-mixable. Preferably, they do not damage the virosomes, particularly the membrane fusion proteins present in these. More preferably, the solvents are pharmaceutically acceptable and non-toxic. Preferred solvents are azeotropic solvents, alcohols and esters.

The volume of dissolved adjuvant is typically small as compared to the volume of aqueous virosome composition into which it is diluted. For example, the adjuvant solution is diluted at least 5-fold, preferably at least 10-fold, more preferably at least 20-fold.

Hence, the water solubility of the adjuvant solvent can be relatively low. In one embodiment, the non-aqueous adjuvant solvent has a solubility in water of at least 5 g/100 mL at 20° C. Preferably, the solubility in water at 20° C. is at least 10 g/100 mL, more preferably at least 20 g/100 mL. In a preferred embodiment, the adjuvant solvent is a water miscible solvent i.e. a solvent that mixes with water in all proportions, forming a homogeneous solution.

In one embodiment, the adjuvant solvent is selected from the group consisting of acetonitrile, 2-butanol, methyl acetate, ethyl acetate, acetic acid, formic acid, methanol, ethanol, DMSO, DMF, n-propanol, isopropanol, 2-methyl-1-propanol and THF, or any mixture thereof. To ensure that the fusogenic activity of the virosomes is maintained, the selected adjuvant solvent should preserve at least partially the function of the membrane fusion proteins. The susceptibility of a fusion protein to adverse effects of a solvent will depend on the specific type of fusion proteins. Generally speaking, fusion proteins that induce fusion at low pH are not very sensitive to solvents such as DMSO or DMF, but are very sensitive to acidic solvents, whereas fusion proteins that function at neutral pH, such as the paramyxovirus F protein, are much less sensitive to the pH of solvents The skilled person will be able to test and evaluate the effect of a given non-aqueous solvent on a fusion protein using methods known in the art. For example, a panel of candidate solvents can be screened for its influence on the fusogenic activity of a given virosome preparation in cell-free fusion assays using liposomal targets. Fusion can be monitored by in vitro fusion measurements e.g. by fluorescence resonance energy transfer (FRET) (Struck et al. (1981) Biochemistry 20:4093). Good results can be obtained when the adjuvant solvent is DMSO, ethanol or DMF.

The term "adjuvant" as used herein refers to any substance which, when injected together with one or more antigens, non-specifically enhances the immune response to that antigen(s). Depending on the nature of the adjuvant it can promote a cell-mediated immune response, a humoral immune response or a mixture of the two. Since the enhancement of the immune response is non-specific, it is well understood in the field that the same adjuvant can be used with different antigens to promote responses against different targets e.g., with an antigen from *M. tuberculosis* to promote immunity against *M. tuberculosis* or with an antigen derived from a tumor, to promote immunity against tumors of that specific kind. Adjuvants are herein intended to include any substance or compound that, when used, in combination with an antigen, to immunize a human or an animal, stimulates the immune system, thereby affecting, provoking, enhancing or facilitating the immune response against the antigen, preferably without generating a specific immune response to the adjuvant itself. The term "amphiphilic adjuvant" is intended to include any adjuvant, including compounds like lipopeptides, mono-phosphoryl lipid A and derivatives and analogues thereof, and glycolipids, having hydrophobic membrane embedded and environment oriented polar (head group) moieties and which can associate with, or more preferably integrate into lipid bilayer vesicles or micelles in water. Preferably, the fusion protein, the amphiphilic adjuvant and preferably also the optional further antigen interact with the hydrophobic interior of the lipid bilayer, i.e. are associated with, integrated into, and/or embedded in the bilayer of the viral membrane through hydrophobic interactions with the lipids of the bilayer and/or each other.

The virosomal membranes of the invention are preferably functionally virosomes comprising lipids, an amphiphilic adjuvant, a viral fusion protein and one or more antigens, wherein the amphiphilic adjuvant, lipids, viral fusion proteins and antigens interact primarily through hydrophobic interactions, wherein the hydrophobic part of the amphiphilic adjuvant preferably forms an integral part of a lipid bilayer membrane, which bilayer further contains the fusion protein, antigen(s) and lipids. By functional reconstitution is meant, that the reconstituted membrane has membrane fusion activity. A preferred reconstituted viral membrane is in the form of a vesicle.

The term also includes any amphiphilic adjuvant that is stably incorporated into lipid bilayers (comprising the natural lipids of a virus) with its hydrophobic moiety in contact with the interior, hydrophobic region of the bilayer membrane, and its polar head group moiety oriented toward the exterior, polar surface of the membrane. However, more hydrophobic adjuvants having a less pronounced amphiphilicity, i.e. having no or only weakly polar head group moieties, but which can associate with, or integrate into lipid bilayer vesicles, are specifically not excluded from the invention.

Adjuvants are herein intended to include any substance or compound that, when used, in combination with an antigen, to immunise a human or an animal, stimulates the immune system, thereby provoking, enhancing or facilitating the immune response against the antigen, preferably without generating a specific immune response to the adjuvant itself. Preferred adjuvants skew the immune response from a Th2 type response to a Th1 type response. Other preferred adjuvants enhance the immune response against a given antigen by at least a factor of 1.5, 2, 2.5, 5, 10 or 20, as compared to the immune response generated against the antigen under the same conditions but in the absence of the adjuvant. Other preferred adjuvants enhance the duration of the immune response. Tests for determining the statistical average enhancement of the immune response against a given antigen as produced by an adjuvant in a group of animals or humans over a corresponding control group are available in the art. The adjuvant preferably is capable of affecting or enhancing the immune response against at least two different antigens. The adjuvants to be incorporated in the functionally virosomes of the invention are preferably amphiphilic adjuvants.

In a preferred embodiment, the amphiphilic adjuvant present in the virosome is pharmaceutically acceptable for use in humans. The amphiphilic adjuvants of the invention are preferably not covalently linked to the antigens but are present together in the lipid bilayer of the reconstituted membrane. The fact that the antigen and adjuvant are not covalently linked assures that processing of the antigen and presentation of its epitopes to the immune system is essentially identical to that of the natural protein alone, ensuring good recognition of the protein present on the natural pathogen. On the other hand, the hydrophobic interaction of the antigen and the adjuvant with the lipid bilayer (and each other) allows for a distribution of the adjuvant and antigen over the virosomes in a preparation whereby the majority of the membrane vesicles in a preparation contain both the antigen and adjuvant in a single vesicle, more preferably at least 60, 70, 80, 90, or 95% of the vesicles contain both the antigen and adjuvant. The combination of antigen and adjuvant in a single membrane or vesicle allows delivery of the antigen to the antigen presenting cell that is activated by the adjuvant, thereby increasing the therapeutic and/or prophylactic efficacy of the virosomes.

In a preferred embodiment of the invention said amphiphilic adjuvant is recognized by a Toll-like-receptor (TLR) present on antigen presenting cells. Alternatively, the amphiphilic adjuvants may target other receptors. Various compounds recognized by TLR's are known in the art and include e.g. lipopeptides, mono-phosphoryl lipid A and derivatives or synthetic or semi-synthetic analogues of mono-phosphoryl lipid A, lipopolysaccharides, peptidoglycans, lipoteichoic acids, lipoproteins (from mycoplasma, mycobacteria or spirochetes), double-stranded RNA (poly I:C), unmethylated DNA, lipoarabinomannan, flagellin, CpG-containing DNA, and imidazoquinolines. Such TLR-recognized adjuvants may be amphiphilic adjuvants by themselves, or alternatively they may be modified into an amphiphilic adjuvant, e.g. by conjugation of hydrophobic compounds (see below) to a polar TLR ligand. Preferred amphiphilic adjuvants include mono-phosphoryl lipid A and derivatives thereof and lipopeptide.

In one embodiment, a virosome of the invention is characterized by the presence of a synthetic adjuvant selected from PHAD (phosphorylated hexaacyl disaccharide) and the 3-O-desacyl derivate thereof, 3-D-PHAD. Both are known in the art as synthetic TLR-4 agonists. PHAD is also referred to in the art as Glycopyranoside Lipid A, or GLA. See Lousada-Dietrich et at, Vaccine. 2011 Apr. 12; 29(17):3284-92. In one embodiment, the virosome contains PHAD, which has the following structure (designations 14 indicate the total number of carbon atoms in each acyl chain):

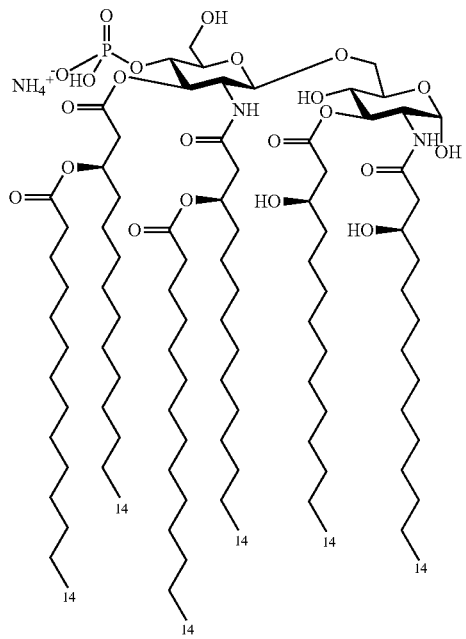

In another preferred embodiment, the virosome contains 3-D-PHAD which has the following structure:

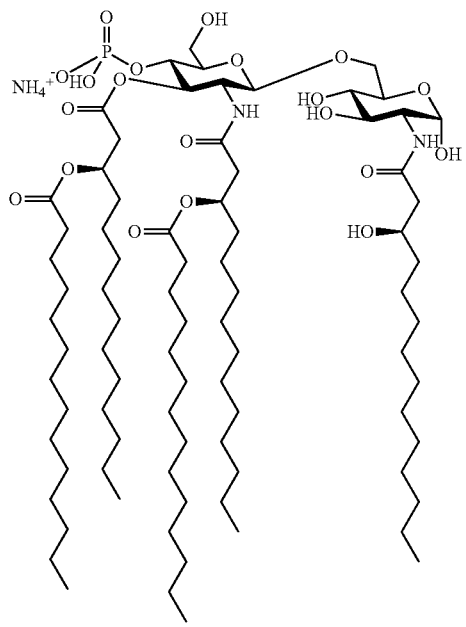

In another embodiment of the invention said amphiphilic adjuvant is a glycolipid. A preferred glycolipid for use as amphiphilic adjuvant has adjuvant activity and is pharmaceutically acceptable for use in humans. Glycolipids are lipids (or other hydrophobic compounds) covalently coupled to one or more sugars. Exemplary glycolipid adjuvants include α-galactosylceramide, phosphatidylinositol mannoside, derivates of endotoxic lipopolysaccharides and derivatives thereof. In a highly preferred embodiment the invention provides virosomes according to the invention, in which the glycolipid is an α-galactosylceramide or a phosphatidyl inositol mannoside. The terms "an α-galactosylceramide" and "a phosphatidyl inositol mannoside" are intended to include any derivative of either one. Derivatives of these molecules having adjuvant activity and that are useful in the context of the present invention are e.g. described in U.S. Pat. No. 5,936,076 and in U.S. Pat. No. 4,542,212, respectively. Other suitable glycolipid adjuvants for use in the invention include e.g. modified forms of endotoxic lipopolysaccharides (LPS) of Gram-negative bacteria having reduced toxicity of the Lipid A portion the LPS but retaining (part of) the adjuvant activity, as may be obtained from genetically modified Gram negative pathogens and as reviewed in WO02/09746.

A modified LPS for use as amphiphilic adjuvant in the invention preferably has a modified Lipid A moiety with reduced toxicity. The toxicity of a modified LPS preferably is less than the toxicity of a corresponding wild-type LPS, more preferably the toxicity of the modified LPS is less than 90, 80, 60, 40, 20, 10, 5, 2, 1, 0.5 or 0.2% of the toxicity of the wild-type LPS. The toxicities of wild-type and various modified LPS's with reduced toxicity may be determined in any suitable assay known in the art. On the other hand, a modified LPS with reduced toxicity should still have sufficient immunostimulatory activity, i.e. adjuvant activity. The modified LPS with reduced toxicity preferably has at least 10, 20, 40, 80, 90 or 100% of the immunostimulatory activity of the corresponding wild-type LPS. The immunostimulatory activity may be determined in vivo in laboratory animals as described above, or in vitro, e.g. by determining the maturation of dendritic cells stimulated by incubation with the LPS to be tested by measuring the production of at least one cytokine (e.g. one of IL-12, IL-10, TNF-alpha, IL-6 and IL-1-beta) by the LPS-stimulated dendritic cells, or by measuring the expression of at least one co-stimulatory molecule (e.g. CD40 or CD86) on the LPS-stimulated dendritic cells.

In another aspect of the present invention, the amphiphilic adjuvant present in the virosome according to the invention, is a peptide, preferably an amphiphilic peptide. A preferred peptide for use as amphiphilic adjuvant has adjuvant activity and is pharmaceutically acceptable for use in humans. Peptides, in particular polar peptides, with adjuvant activity may be rendered into amphiphilic adjuvants by (covalently) linking them to a suitable hydrophobic compound (see above). Alternatively, amphiphilic peptides may comprise a hydrophobic stretch of amino acids such as a transmembrane sequence as described below. A preferred peptide comprises a sequence from the Notch ligand Jagged-1 (see Weijzen et al., 2002; Genbank accession no. AAC 52020) or a sequence from the *Staphylococcus aureus* protein A. Peptides having sequences from Jagged-1 or protein A are preferably covalently coupled to a suitable hydrophobic compound (see above) and/or comprise a transmembrane sequence (see below). The (polar) part of the Jagged-1 or protein A derived peptides that protrudes from the lipid bilayer preferably comprises no more than 3, 4, 5, 6, 7, or 8, amino acids.

The virosomes of the invention comprise a fusion protein and, optionally further antigens. Thus, it is to be understood that the virosomes comprising only a viral fusion protein and no further antigens are a part of the invention, in which case the viral fusion protein also has a function as antigen, in addition to its function as fusion protein. On the other hand, the virosomes may thus comprise one or more further antigens in addition to the viral fusion protein. Accordingly, in one embodiment the virosome comprises at least one further antigen, preferably a tumor-antigen or an antigen originating from a virus, a parasite, a fungus or a bacterium.

The antigens that are part of the reconstituted viral membrane according to the invention preferably have a hydrophobic part that is capable of being inserted in the lipid bilayer membrane of the reconstituted viral membrane vesicle. Many pathogenic entities such as viruses, bacteria, yeasts and parasites carry in their capsid, cell wall or membrane, proteins that elicit an immune response in the host. Examples of antigens that have hydrophobic elements, such as e.g. transmembrane segments, and that are suited to be part of a reconstituted viral membrane according to the invention are proteins present in the membrane (also called envelope in the case of viruses) of the pathogen. Therefore, in preferably, the antigen present in the reconstituted viral membrane of the invention is an integral membrane protein. The antigenic proteins in the virosomes of the present invention are oriented in the same way as they appear on the viral or cellular membrane, but may present epitopes that are normally partially or at least temporarily hidden when present in a membrane lipid bilayer. Stimulation of the immune system by these antigen-presenting virosomes may be due to a combination of their specific recognition by cells of the immune system, their particular character, the presentation of the protein, and the uncovering of hidden epitopes. Preferably, the antigenic proteins that are used in the virosomes of the invention comprise one or more protective epitopes, i.e. epitopes capable of eliciting an immune response in a mammal that provides protection against infection by the pathogen from which the antigen is derived, or that provides protection against a tumor expressing the antigen.

In preferred embodiments, said antigens are derived from a virus, a parasite, a fungus or a bacterium. Antigens that can be applied and used in the formation of the virosomes according to the invention can be derived from all sorts of viruses, non-limiting examples of such viruses are: Retroviridae such as Human Immunodeficiency virus (HIV); a rubellavirus; paramyxoviridae such as parainfluenza viruses, measles, mumps, respiratory syncytial virus (RSV), human metapneumovirus; flaviviridae such as yellow fever virus, dengue virus, Hepatitis C Virus (HCV), Japanese Encephalitis Virus (JEV), tick-borne encephalitis, St. Louis encephalitis or West Nile virus; Herpesviridae such as Herpes Simplex virus, cytomegalovirus, Epstein-Barr virus; Bunyaviridae; Arenaviridae; Hantaviridae such as Hantaan; Coronaviridae; Papovaviridae such as human Papillomavirus; Rhabdoviridae such as rabies virus. Coronaviridae such as human coronavirus; Alphaviridae, Arteriviridae, filoviridae such as Ebolavirus, Arenaviridae, poxviridae such as smallpox virus, and African swine fever virus. Especially preferred are virosomes, wherein said antigen is derived from influenza virus or RSV. Proteins from influenza virus that can be used in virosomes of the present invention are preferably the hemagglutinin (HA) protein, the neuraminidase (NA) protein and/or the M2 protein, alone or in combination. Proteins from RSV that can be used in virosomes of the current invention are the fusion (F), glycoprotein (G) and/or matrix (M) protein.

Likewise such antigens may be derived from pathogenic bacteria, fungi (including yeasts), or parasites. Such antigens include bacterial antigens of e.g. *Helicobacter*, such as *H. pylori*, *Neisseria*, such as *N. mengitidis*, *Haemophilus*, such as *H. influenza*, *Bordetella*, such as *B. pertussis*, *Chlamydia*, *Streptococcus*, such as *Streptococcus* sp. serotype A, *Vibrio*, such as *V. cholera*, Gram-negative enteric pathogens including e.g. *Salmonella*, *Shigella*, *Campylobacter* and *Escherichia*, as well as antigen from bacteria causing anthrax, leprosy, tuberculosis, diphtheria, Lyme disease, syphilis, typhoid fever, and gonorrhea. Antigens from parasites e.g. include antigens from protozoans, such as *Babeosis bovis*, *Plasmodium*, *Leishmania* spp. *Toxoplasma gondii*, and *Trypanosoma*, such as *T. cruzi*. Fungal antigens may include antigens from fungi such as *Aspergillus* sp., *Candida albicans*, *Cryptococcus*, such as e.g. *C. neoformans*, and *Histoplasma capsulatum*.

Although vaccination is generally applied for the prophylactic protection against pathogens or for the treatment of diseases following pathogenic infection, the person skilled in the art is aware of the application of vaccines for tumor-treatment. Moreover, an increasing number of tumor-specific proteins are found to be proper entities that can be targeted by human or humanized antibodies. Such tumor-specific proteins are also within the scope of the present invention. Many tumor specific antigens are known in the art. Therefore, in one preferred embodiment, the present invention provides virosomes comprising a tumor-specific antigen. Suitable tumor antigens include e.g. carcinoembryonic antigen, prostate-specific membrane antigen, truncated epidermal growth factor receptor (EGRF), Thomsen-Friedenreich (T) antigen, GM-2 and GD-2 gangliosides, Ep-CAM, mucin-1, epithelial glycoprotein-2, and colon specific antigen.

Preferred antigens from these pathogens are integral membrane proteins. However, non-membrane protein antigens or parts thereof containing protective epitopes may also be modified for use in the present invention fusing them to a transmembrane sequence. Hence, in one embodiment the antigen is an integral membrane protein or an antigen attached to a membrane anchoring moiety. For example, the antigen can be attached to a transmembrane domain or membrane-anchoring amino acid sequence. Transmembrane sequences or membrane-anchoring sequences are well known in the art and are based on the genetic geometry of mammalian transmembrane molecules. A transmembrane sequence usually consists of a stretch of about 10-30, usually around 20 amino acids, the majority of which having hydrophobic side chains. Transmembrane sequences are known for a wide variety of proteins and any of these may be used. Examples of membrane-anchoring sequences for use in the present invention include e.g. those derived from CD8, ICAM-2, IL-8R, CD4 and LFA-1. Preferably a transmembrane sequence is derived from viral integral membrane protein that is naturally present in a viral membrane. Examples thereof include the transmembrane region of human respiratory syncytial virus (RSV) glycoprotein G (e.g. amino acids 38 to 63) or the transmembrane region of influenza virus neuraminidase (e.g. amino acids 7 to 27). Hydrophobic interactions result from non-covalent, non-electrostatic attraction forces between hydrophobic substances that are present in an aqueous environment. In one embodiment, the membrane anchoring moiety is a lipid moiety, preferably a phospholipid or acyl chain. Accordingly, further preferred antigens are soluble proteins or peptides that are covalently linked to hydrophobic substances such as phospholipids or acyl chains, allowing their incorporation in the virosomal membrane.

The invention also provides an adjuvanted virosome obtainable by the novel "post-insertion" method according to the invention. Such adjuvanted virosome is among others characterized in that the adjuvant is an amphiphilic adjuvant which is essentially confined to the outer leaflet of the virosomal membrane. Preferably, the adjuvanted virosome comprises one or more of the amphiphilic adjuvants described herein above. Particularly preferred virosomes are those derived from an enveloped virus, preferably a virus selected from the group consisting of Retroviridae; rubellavirus; paramyxoviridae; Flaviviridae; Herpesviridae; Bunyaviridae; Arenaviridae; Hantaviridae; Baculoviridae; Coronaviridae; Papovaviridae; Rhabdoviridae; Alphaviridae, Arteriviridae, Filoviridae and Poxviridae.

The adjuvanted virosome may comprise at least one further antigen, preferably a tumor-antigen or an antigen originating from a virus, a parasite, a fungus or a bacterium. In a specific embodiment, the antigen is a viral antigen, preferably derived from influenza virus or RSV. As described herein above, the antigen can be an integral membrane protein or an antigen attached to a membrane anchoring moiety, preferably wherein the membrane anchoring moiety is a transmembrane domain, a membrane-anchoring amino acid sequence or a lipid moiety.

Other specifically preferred virosomes are those which include antigens from human metapneumovirus, paramyxovirus F proteins, the Herpes Simplex virus gD and gB proteins, influenza virosomes additionally containing proteins or peptides derived from the HIV gp41 protein, influenza virosomes containing proteins and peptides from malaria proteins such as CS and AMA, or influenza virosomes additionally containing antigen useful in breast cancer vaccines.

The virosomes according to the invention may be used to deliver a substance (e.g. an immunogenic molecule, a drug and/or a gene) to a target cell. Unlike liposomes, virosomes offer the advantage of efficient entry into the cells triggered by the viral envelope protein, followed by the intracellular release of the virosomal contents. Moreover, if certain active viral envelope proteins are incorporated into their membranes, the virosomes may release their contents into the cytoplasm immediately after fusion with a cell membrane, e.g. hereby preventing the degradation of the therapeutic substance in the acidic environment of the endosome.

The virosomes according to the invention are especially useful in the field of vaccination, where it is desired to stimulate an immune response to an antigen associated with a particular disease or disorder. In such cases, the antigen is typically encapsulated in or bound to the virosome, which then delivers this antigen to the host immune system to be vaccinated. By virtue of the particular antigen delivered, the resulting prophylactic and/or therapeutic is necessarily specific for the disease or disorder with which the antigen is associated.

In a further aspect the present invention therefore provides for a pharmaceutical preparation comprising as active ingredient virosomes according to the invention, and a pharmaceutically acceptable carrier, diluent or excipient. Pharmaceutically acceptable stabilizing agents, osmotic agents, buffering agents, dispersing agents, and the like may also be incorporated into the pharmaceutical compositions. The preferred form depends on the intended mode of administration and therapeutic application. The pharmaceutical carrier can be any compatible, non-toxic substance suitable to deliver the virosomes to the patient.

Pharmaceutically acceptable carriers for intranasal delivery are exemplified by water, buffered saline solutions, glycerin, polysorbate 20, cremophor EL, and an aqueous mixture of caprylic/capric glyceride, and may be buffered to provide a neutral pH environment. Pharmaceutically acceptable carriers for parenteral delivery are exemplified by sterile buffered 0.9% (w/v) NaCl or 5% (w/v) glucose optionally supplemented with a 20% albumin. Preparations for parental administration must be sterile. The parental route for administration of the polypeptide or antibody is in accord with known methods, e.g. injection or infusion by intravenous, intraperitoneal, intramuscular, intra-arterial or intralesional routes.

A typical pharmaceutical composition for intramuscular injection would be made up to contain, for example, 1-10 ml of phosphate buffered saline and 1 to 100 µg, preferably 15-50 µg (of antigen protein) of the virosomes of the present invention.

For oral administration, the active ingredient can be administered in liquid dosage forms, such as elixirs, syrups, and suspensions. Liquid dosage forms for oral administration can contain coloring and flavoring to increase patient acceptance. Methods for preparing parenterally, orally or intranasally administrable compositions are well known in the art and described in more detail in various sources, including, for example, Remington's Pharmaceutical Science (15th ed., Mack Publishing, Easton, Pa., 1980) (incorporated by reference in its entirety for all purposes).

In one embodiment, the virosomes of the invention are comprised in an immunogenic composition or a vaccine. The term "vaccine" refers to a preparation that may be administered to a host to induce a cellular and/or antibody immune response. Vaccines may contain additional adjuvants, pharmaceutically acceptable carriers, diluents or excipients. Exemplary further adjuvants include Complete Freund's Adjuvant, Incomplete Freund's Adjuvant, Gerbu adjuvant (GMDP; C.C. Biotech Corp.), RIBI fowl adjuvant (MPL; RIBI Immunochemical Research, Inc.), potassium alum, aluminum phosphate, aluminum hydroxide, QS21 (Cambridge Biotech), Titer Max adjuvant (CytRx), and Quil A adjuvant. Other compounds that may have adjuvant properties include binders such as carboxymethylcellulose, ethyl cellulose, microcrystalline cellulose, or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin, a flavoring agent such as peppermint, methyl salicylate or orange flavoring, and a coloring agent.

In one embodiment the virosomes of the current invention may be lyophilized, or re-hydrated after lyophilization. Lyophilized virosomes may be used as vaccines as a dry powder or after rehydration.

Also provided is an adjuvanted virosome according to the invention for use as medicament. For example, provided herein is an adjuvanted virosome for use in a method of prophylaxis or treatment of cancer or an infectious disease. In one embodiment, the adjuvanted virosome is immunogenic. The term "immunogenic" refers to a molecule that is capable of eliciting an immune response in a host animal, including producing an antibody response and/or a cell mediated immune response (for example, involving cytotoxic T lymphocytes (CTL)).

The dosage of the adjuvanted virosome or vaccine can be determined by, for example, first identifying doses effective to elicit a prophylactic and/or therapeutic immune response.

This may be accomplished by measuring the serum titer of virus specific immunoglobulins and/or by measuring the inhibitory ratio of antibodies in serum samples, urine samples, and/or mucosal secretions. The dosages can be determined from animal studies, including animals that are not natural hosts to RSV. For example, the animals can be dosed with a vaccine candidate, to partially characterize the immune response induced, and/or to determine if any neutralizing antibodies have been produced. In addition, routine human clinical studies can be performed to determine the effective dose for humans. Effective doses may be extrapolated from dose-response curves derived from in vitro and/or in vivo animal models.

In one embodiment, the daily dose of the medicament prepared according to the invention varies over a range of 10 ng/kg to about 10 g/kg of virosomes per adult per day. For oral administration, the medicament is preferably provided in the form of tablets containing from 0.001 to 1,000 mg, preferably 0.01 to 100 mg, more preferably 0.05 to 50 mg, and most preferably 0.1 to 20 mg of virosome for the symptomatic adjustment of dosage according to signs and symptoms of the patient in the course of treatment. The tablets may e.g. contain 0.001, 0.01, 0.05, 0.1, 0.5, 1, 2.5, 10, 20, 50, or 100 milligrams of virosome. An effective amount of virosome in the medicament prepared according to an embodiment is ordinarily supplied at a dosage level of from about 0.0001 mg/kg to about 50 mg/kg of body weight per dosage unit. More particularly, the range is from about 0.0001 mg/kg to 7 mg/kg of body weight per day. If given to children, the dosage may be reduced appropriately.

Vaccines may in one embodiment be formulated using a diluent. Exemplary "diluents" include water, physiological saline solution, human serum albumin, oils, polyethylene glycols, glycerine, propylene glycol or other synthetic solvents, antibacterial agents such as benzyl alcohol, antioxidants such as ascorbic acid or sodium bisulphite, chelating agents such as ethylene diamine-tetra-acetic acid, buffers such as acetates, citrates or phosphates and agents for adjusting the osmolarity, such as sodium chloride or dextrose. Exemplary "carriers" include liquid carriers (such as water, saline, culture medium, saline, aqueous dextrose, and glycols) and solid carriers (such as carbohydrates exemplified by starch, glucose, lactose, sucrose, and dextrans, antioxidants exemplified by ascorbic acid and glutathione, and hydrolyzed proteins.

Vaccines may in one embodiment contain an excipient. The term "excipient" refers herein to any inert substance (e.g., gum arabic, syrup, lanolin, starch, eta) that forms a vehicle for delivery of an antigen. The term excipient includes substances that, in the presence of sufficient liquid, impart to a composition the adhesive quality needed for the preparation of pills or tablets.

In one embodiment, the immune response comprises production of an antibody that specifically binds to the protein of interest that is comprised in the virosome. The terms "specific binding" or "specifically binding" when used in reference to the interaction of an antibody or cell (such as a lymphocyte cell) with another molecule (such as a protein or peptide), means that the interaction is dependent upon the presence of a particular structure (i.e., the antigenic determinant or epitope) on the molecule.

In another embodiment, the immune response comprises increasing the number of T lymphocytes that specifically bind to the protein of interest. The term "T lymphocytes" includes, but is not limited to, one or more of cytotoxic T cells (CTLs), helper T cells, and suppressor T cells. T lymphocytes express receptors that recognize antigen in the form of peptide fragments complexed with MHC molecules.

Thus, the invention's virosomes may in one embodiment be incorporated into vaccines, and an immunologically effective amount of the vaccine may be administered to an animal to produce an immune response. As used herein the terms "immunogenically effective amount" and "immunologically effective amount" refer to that amount of a molecule that elicits and/or increases production of an immune response (including production of specific antibodies and/or induction of a TCL response) in a host upon vaccination. It is preferred, though not required, that the immunologically-effective (i.e., immunogenically-effective) amount is a "protective" amount. The terms "protective" and "therapeutic" amount of a composition refer to an amount of the composition that delays, reduces, palliates, ameliorates, stabilizes, and/or reverses one or more symptoms of a disease.

The invention's virosomes or vaccines may be in one embodiment administered prophylactically (i.e., before infection with an infectious agent and/or the observation of disease symptoms) and/or therapeutically (i.e., after infection with an infectious agent and/or the observation of disease symptoms). Administration also may be concomitant with (i.e., at the same time as, or during) manifestation of one or more disease symptoms. Also, the invention's virosomes or vaccines may be administered before, concomitantly with, and/or after administration of another type of drug or therapeutic procedure (e.g., surgery, chemotherapy, radiotherapy, etc.). Methods of administering the invention's compounds include, without limitation, administration in parenteral, oral, intraperitoneal, intranasal, topical (e.g., rectal, and vaginal), and sublingual forms. Parenteral routes of administration include, for example, subcutaneous, intravenous, intramuscular, intrastemal injection, and infusion routes. In a further aspect, the invention relates to a method for vaccination against, or for prophylaxis or therapy of an infectious disease or tumor by administration of a therapeutically or prophylactically effective amount of (a pharmaceutical composition comprising) virosomes of the invention to a subject in need of prophylaxis or therapy. The invention also relates to virosomes of the invention for use as a medicament, preferably a medicament for vaccination against, or for prophylaxis or therapy of an infectious disease or tumor. The invention further relates to the use of virosomes of the invention in the manufacture of a medicament for vaccination against, or for prophylaxis or therapy of an infectious disease or tumor. In one embodiment, the invention provides a method for immunizing a subject against cancer or a viral disease, comprising administering to the subject an immunologically effective amount of an immunogenic composition of the invention to produce an immune response. For example, the viral disease is caused by RSV, influenza virus, herpes virus, or cytomegalovirus.

A still further aspect relates to the area of drug development, in particular vaccine optimization. Provided is a method for optimizing the adjuvant/antigen ratio of a virosome-based vaccine, comprising preparing at least two preparations comprising adjuvanted virosomes according to the invention and/or using the "post-insertion" method according to the invention, each preparation having a distinct adjuvant/antigen ratio, and evaluating each preparation in a test subject for its efficacy in inducing an immune response. As explained herein above, this method has important advantages for the preclinical and clinical testing of vaccines comprising adjuvanted virosomes. Since the preformed virosome composition forms "drug substance A", while the adjuvant in the solvent is "drug substance B', only the safety and clinical testing for drug substance A and B is required. The combination of substances A and B into the at least two drug product preparations with distinct adjuvant/ antigen ratios can take place at the bedside, thus obviating expensive safety evaluations of each individual adjuvant/ antigen ratio in preclinical and then in clinical trials. Moreover, the method allows for different adjuvants to be tested with any virosome, or any adjuvant to be tested economically with different virosomes.

LEGENDS TO THE FIGURES

Figure 1B:
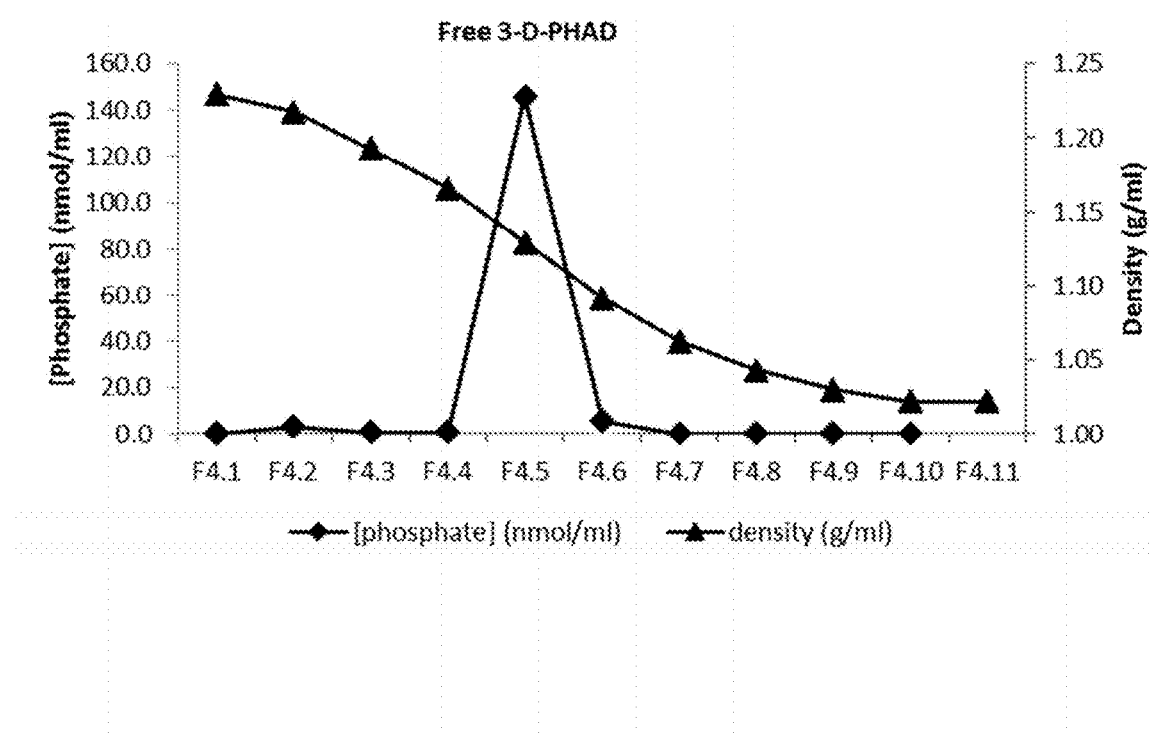

FIG. 1: Equilibrium density gradient analysis of post-inserted adjuvant 3-D-PHAD in RSV virosomes. Panel A shows the protein, phosphate (from both phospholipids and 3-D-PHAD), and density in fractions numbered 1.1, 1.2 consecutively through 1.11 from bottom to top; Panel B shows a similar gradient of only 3-D-PHAD dissolved in DMSO.

Figure 2:
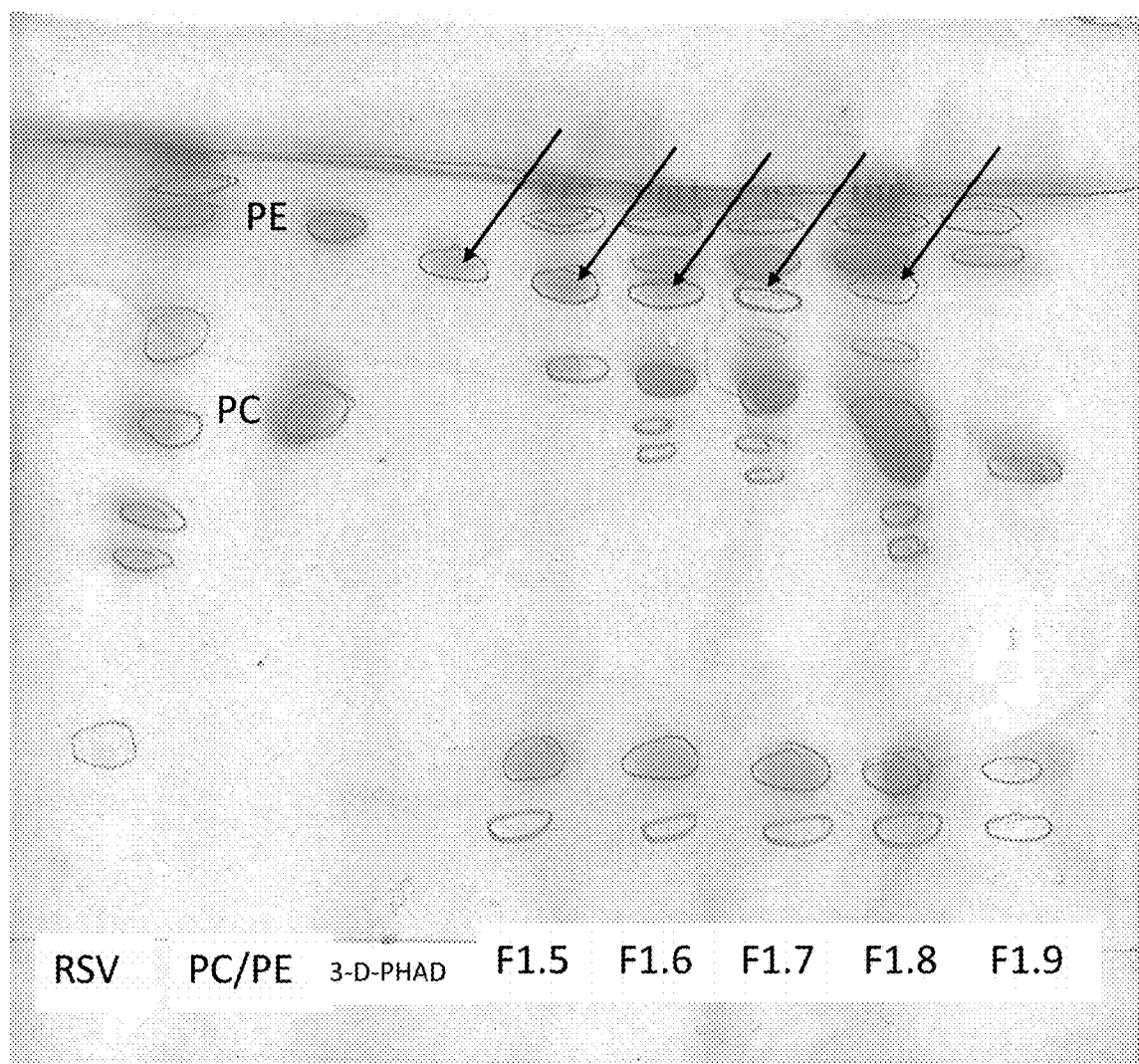

FIG. 2: TLC plate analysis of samples from the gradient of FIG. 1A. lane 1: RSV viral lipid extract; lane 2: the PC and PE that were used; lane 3: 3D-PHAD adjuvant; lanes 4-8: fractions 1.5-1.9 of the gradient. Spots were circled after ethanol stain and the plate was developed with phosphomolybdate reagent.

Figure 3:
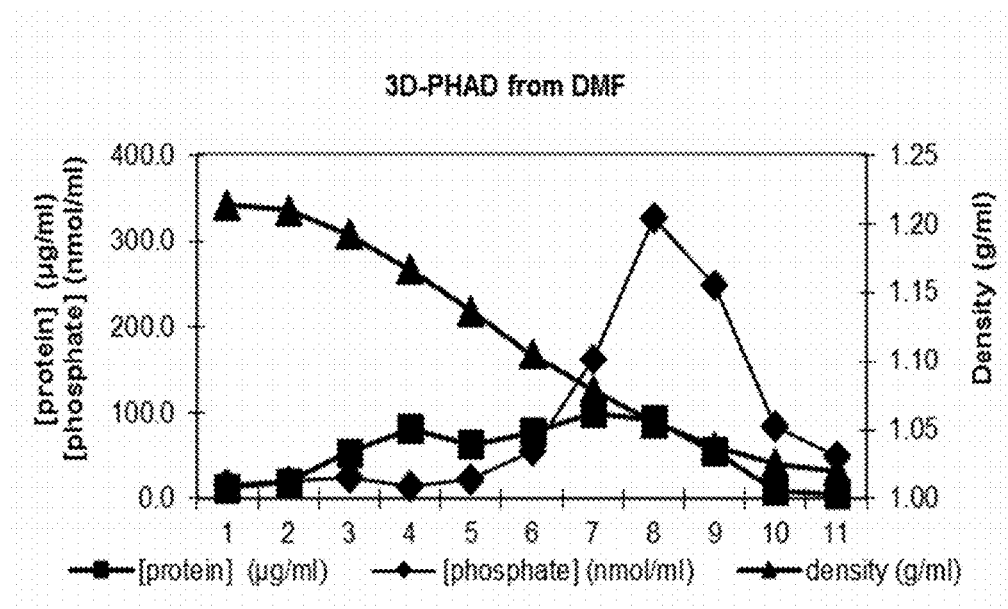

FIG. 3: Equilibrium density gradient analysis of the post-insertion of the adjuvant 3-D-PHAD in RSV virosomes from a solution in DMF. The fractions are numbered from bottom to top. Analysis as in FIG. 1.

Figure 4:
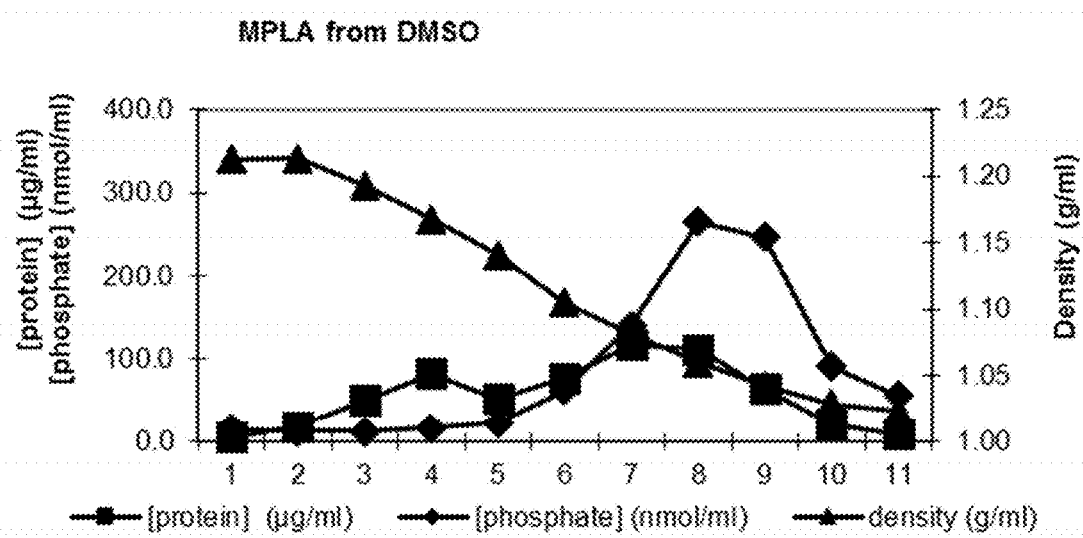

FIG. 4: Equilibrium density gradient analysis of the post-insertion of the adjuvant MPLA in RSV virosomes from a solution in DMSO. The fractions are numbered from bottom to top. Analysis as in FIG. 1.

Figure 5:
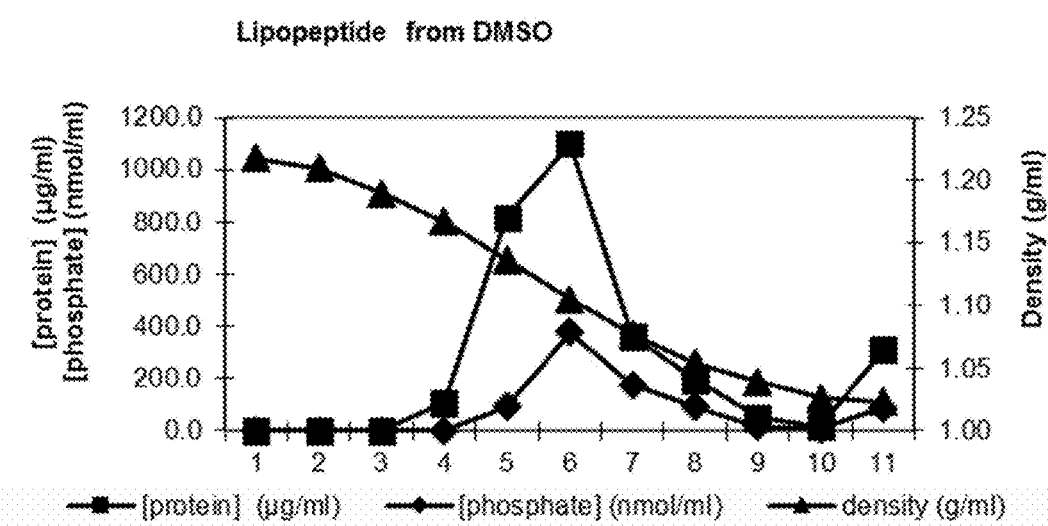

FIG. 5: Equilibrium density gradient analysis of the post-insertion of the lipopeptide adjuvant in RSV virosomes from a solution in DMSO. The fractions are numbered from bottom to top. Analysis as in FIG. 1.

Figure 6:
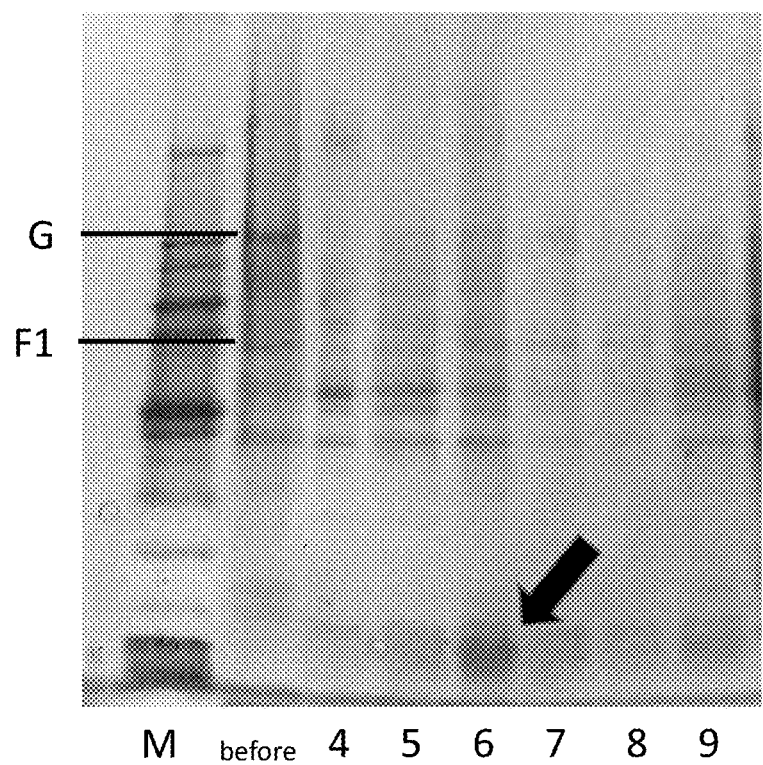

FIG. 6: Silver-stained SDS-PAGE gel of samples from the fractions of the gradient in FIG. 5. The viral membrane proteins F (F1 subunit) and G are indicated. The lipopeptide is marked with an arrow.

Figure 7:
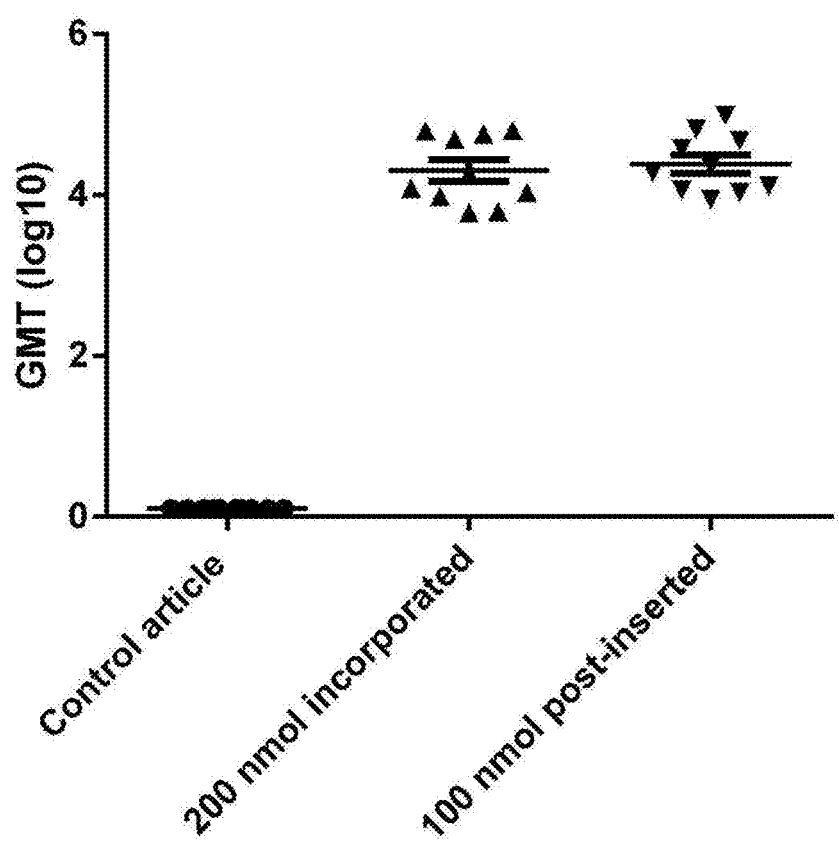

FIG. 7: Anti-RSV IgG as determined by ELISA. Logarithmic (base 10) representation of the geometric mean titer, the line denoting the average.

Figure 8:
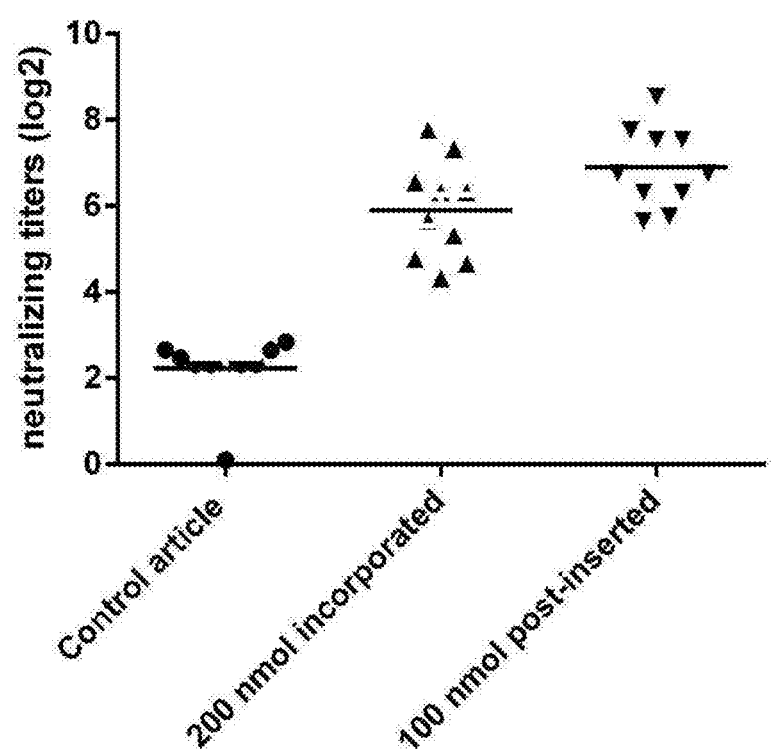

FIG. 8: Ex-vivo neutralizing antibodies. Logarithmic (base 2) representation of the titer, the line denoting the average.

EXAMPLES

Example 1: Incorporation of the Adjuvant MPL by Post-Insertion into RSV Virosomes Virosomes were prepared from purified respiratory syncytial virus (RSV), strain A2, as described in the art. Briefly, the virus was solubilized in 50 mM di-caproylphosphatidylcholine (DCPC) for 30 min on ice, and the viral nucleocapsids were removed by centrifugation at 120 000 g for 30 min. The supernatant was collected and filtered through an 0.1 µm filter. A thin lipid film was prepared from a mixture of phosphatidylcholine (PC) and phosphatidylethanolamine (PE) (source: chicken egg, respectively transphosphatidylated from chicken egg) at a 2:1 molar ratio by evaporation of the solvent (chloroform/methanol 2:1 v/v). The viral membrane supernatant (2.35 ml) was added to the thin lipid film at a ratio of 1 mg of protein per 850 nmol of phospholipid. The mixture was filtered through an 0.2 µm filter and dialyzed in a slide-a-lyzer dialysis cassette, sterilized by gamma irradiation, 10 kDa molecular weight cut-off, for 48 hours against 7 changes of 2 liters of HNE buffer, at 4° C. The virosomes were harvested and the phospholipid concentration in the virosomes was measured.

Stock solutions of the synthetic mono-phosphoryl lipid A analogue 3-D-PHAD (disclosed in WO2013/155448), an amphiphilic adjuvant, in DMSO were prepared. To 975 µl of virosomes, containing 850 nmol of phospholipids, 25 µl of DMSO solution containing 153 nmol of 3-D-PHAD was rapidly added while agitating the sample on a vortex mixer. After overnight storage at 4° C., the density of the virosomes was analyzed by equilibrium density gradient centrifugation loaded on 10-60% sucrose gradients, which were spun for 66 hrs in a Sorvall AH 650 rotor at 50 krpm. As a control, 153 nmol of 3 D-P-HAD alone was also run on a similar gradient. Samples from the gradient were analyzed for sucrose concentration by refractometry, giving a measure of density, phosphate (both lipid and 3-D-PHAD), and protein. As shown in FIG. 1, the virosomes formed a single band around 1.054-1.0759 g/ml, containing all phosphate, while free 3-D-PHAD banded around 1.12 g/ml. Therefore, most of the 3 D PHAD added to the virosomes from a DMSO solution was incorporated into the virosomes.

Fractions of the gradient were extracted with chloroform/methanol according to Folch, and analyzed by thin layer chromatography, on a Merck HP TLC 60 µlate. The plates were run in chloroform:methanol:water 100:75:15 (v/v). Lipids and 3 DPHAD were visualized by consecutive ethanol, iodine, ninhydrin and phosphomolybdate stain. As a control, a Folch extract of RSV viral lipids, the PC and PE used to prepare the virosomes, and free 3 DPHAD were also ran on the same plate. As shown in FIG. 2, 3-D-PHAD was found to present in the virosome-containing fractions.

Example 2: Post-Insertion of Several Adjuvants Using Several Solvents into RSV Virosomes Virosomes were prepared from purified RSV virus, strain A2, as described in example 1. The virosomes were harvested and the phospholipid concentration in the virosomes was measured.

Stock solutions of several adjuvants in several solvents were prepared:
1) 100 nmol 3-D-PHAD in 50 µl DMF
2) 100 nmol mono-phosphoryl lipid A (MPLA) in 50 µl DMSO
3) 0.3 mg N-palmitoyl-S-2,3(bispalmitoyloxy)-propyl-cysteinyl-seryl-(lysil)3-lysine (lipopeptide) in 50 µl DMSO The above adjuvant solutions were added to four tubes with 950 µl of virosomes each, containing 850 nmol of phospholipids, with rapid mixing on a vortex. After overnight storage at 4° C., the density of the virosomes was analyzed by equilibrium density gradient centrifugation on 10-60% sucrose gradients, which were spun for 66 hrs in a Sorvall AH 650 rotor at 120 000 g. Samples from the gradient were analyzed for density, phosphate (both lipid and 3 DPHAD), and protein. As shown in FIGS. 3-5, on all gradients there was but a single peak of phosphate (from phospholipids, 3-D-PHAD or MPLA), also containing protein, whereas the lipopeptide was found to be present in fraction 4-7, peaking at fraction 6 (containing the highest concentration of virosomes) by SDS-PAGE electrophoresis (FIG. 7). This demonstrates that, the adjuvant was incorporated in the virosomes in all cases. While the lipopeptide-containing virosomes have a peak density around 1.1 g/ml, the other virosomes banded at around 1.04-1.06 g/ml. Thus, different adjuvants added to the virosomes affect the density of the virosomes differently, providing further proof of their incorporation.

Example 3: Immunization of Mice with RSV Virosomes Containing 3-D-PHAD Incorporated Either During or after Virosome Formation Two different virosome preparations were prepared from purified respiratory syncytial virus (RSV), strain A2. Briefly, the virus was solubilized in 50 mM di-caproylphosphatidylcholine (DCPC) for 30 min on ice, and the viral nucleocapsids were removed by centrifugation at 120 000 g for 30 min. The supernatant was collected and filtered through an 0.1 µm filter. Two thin lipid films were prepared, one (test sample) from a mixture of PC and PE at a 2:1 ratio by evaporation of the solvent (chloroform/methanol 2:1 (v/v)); the other (comparative example), additionally contained 3-D-PHAD The viral membrane supernatant was added to the thin lipid film at a ratio of 1 mg of protein per 850 nmol of phospholipid (test sample) or 850 of phospholipid plus 200 nmol 3-D-DPHAD (comparative example). The mixture was filtered through an 0.2 µm filter and dialyzed in a slide-a-lyzer dialysis cassette, sterilized by gamma irradiation, 10 kDa molecular weight cut-off, for 48 hours against 7 changes of 2 liters of HNE buffer, at 4° C. The virosomes were harvested and the phospholipid concentration in the virosomes was measured. To 975 µl of the aqueous virosome composition containing 850 nmol of phospholipids and no 3-D-PHAD 25 µl of DMSO solution containing 153 nmol of 3-D-PHAD was rapidly added while agitating the sample on a vortex mixer. Therefore, the comparative virosome preparation contained 200 nmol of 3-D-PHAD incorporated during virosome formation ("incorporated"), while the test virosome preparation contained 100 nmol of 3-D-PHAD added from solvent after virosome formation ("post-inserted").

Three groups of ten Balb/C mice each were immunized at day 1 and 15 with either vehicle control (HNE buffer, 145 mM NaCl, 5 mM HEPES, 1 mM EDTA, pH 7.4), the "incorporated" virosome preparation at 5 µg of viral protein and 1 µg of 3-D-PHAD per mouse per injection, or the "post-inserted" virosome preparation at 5 µg of viral protein and 0.5 µg of 3-D-PHAD per mouse per injection.

IgG titers against viral proteins were determined on day 28, as described before ((Kamphuis, T. et al. Plos One 2012; 7 (5):e36812). As shown in FIG. 7, the IgG titers induced by the 3-D-PHAD post-inserted virosomes were equivalent to those of the incorporated 3-D-PHAD virosomes, while the latter virosomes contained twice the amount of adjuvant.

Neutralizing antibody titers against live virus were determined ex-vivo on day 28, as described before (Kamphuis, T. et al. Plos One 2012; 7 (5):e36812). As shown in FIG. 8, the IgG titers induced by the 3-D-PHAD post-inserted virosomes were at least equivalent to those of the incorporated 3-D-PHAD virosomes, while the latter virosomes contained twice the amount 3-D-PHAD.

The invention claimed is:
1. A method for preparing adjuvanted virosomes, comprising the steps of:
(i) providing an aqueous composition of non-adjuvanted virosomes comprising a membrane fusion protein;
(ii) dissolving an amphiphilic adjuvant in a pharmaceutically acceptable non-aqueous solvent which can form a homogeneous mixture with water; and
(iii) diluting said mixture obtained in step (ii) in said aqueous virosome composition of step (i) to induce insertion of adjuvant in the outer leaflet of the virosomal membrane while preserving membrane fusion activity of the virosomes.

2. The method according to claim 1, wherein said non-aqueous solvent of step (ii) has a solubility in water of at least 5 g/100 mL at 20° C.

3. The method according to claim 2, wherein said non-aqueous solvent is a water miscible solvent.

4. The method according to claim 1, wherein said adjuvant solvent is selected from the group consisting of acetonitrile, 2-butanol, methyl acetate, ethyl acetate, acetic acid, formic acid, methanol, ethanol, DMSO, DMF, n-propanol, isopropanol, 2-methyl-1-propanol and THF, or any mixture thereof.

5. The method according to claim 4, wherein the adjuvant solvent is DMSO.

6. The method according to claim 1, wherein the membrane fusion protein is a viral fusion protein.

7. The method according to claim 6, wherein the membrane fusion protein is an RSV F protein.

8. The method according to claim 1, comprising preparing virosomes by the functional reconstitution of an enveloped virus.

9. The method according to claim 8, wherein said functional reconstitution comprises contacting an enveloped virus with a solution containing a short-chain phospholipid or a detergent allowing solubilisation of the viral envelope of said virus further comprising removing short-chain phospholipid or detergent from said solution allowing formation of a functionally reconstituted viral envelope.

10. The method according to claim 9, wherein said short-chain phospholipid has a critical micelle concentration (cmc) of larger than 0.1 mM.

11. The method according to claim 10, wherein said phospholipid is a phosphatidylcholine.

12. The method according to claim 9, wherein the detergent is octa-ethylene-glycol-mono-N-dodecyl-ether.

13. The method according to claim 1, wherein said amphiphilic adjuvant is mono-phosphoryl lipid A (MPLA) and derivatives thereof.

14. The method according to claim 1, wherein said amphiphilic adjuvant is a glycolipid.

15. The method according to claim 1, wherein said amphiphilic adjuvant is an amphiphilic peptide.

16. The method according to claim 1, wherein the virosome comprises at least one further antigen.

17. The method according to claim 16, wherein the at least one further antigen is a viral antigen.

18. The method according to claim 16, wherein the at least one further antigen is an integral membrane protein or an antigen attached to a membrane anchoring moiety.

19. The method according to claim 18, wherein the membrane anchoring moiety is a transmembrane domain or membrane-anchoring amino acid sequence.

20. The method according to claim 18, wherein the membrane anchoring moiety is a lipid moiety.

21. An adjuvanted virosome obtainable by a method according to claim 1.

22. The adjuvanted virosome according to claim 21, characterized in that the adjuvant is an amphiphilic adjuvant which is essentially confined to the outer leaflet of the virosomal membrane.

23. The adjuvanted virosome according to claim 22, wherein the amphiphilic adjuvant is a compound recognized by a Toll-like receptor (TLR).

24. The adjuvanted Adjuvanted virosome according to claim 21, comprises comprising at least one further antigen, preferably a tumor-antigen or an antigen originating from a virus, a parasite, a fungus or a bacterium.

25. The adjuvanted virosome according to claim 24, wherein the at least one further antigen is a viral antigen.

26. The adjuvanted virosome according to claim 24, wherein the at least one further antigen is an integral membrane protein or an antigen attached to a membrane anchoring moiety.

27. A pharmaceutical composition comprising an adjuvanted virosome according to claim 21, and a pharmaceutically acceptable carrier, diluent or excipient.

28. An immunogenic composition comprising an adjuvanted virosome according to claim 21.

29. The composition according to claim 27, which is formulated for intranasal delivery, parental delivery or oral administration.

30. An adjuvanted virosome according to claim 21 for use as medicament.

31. An adjuvanted virosome according to claim 21 for use in a method of prophylaxis or treatment of an infectious disease.

32. A method for optimizing the adjuvant/antigen ratio of a virosome-based vaccine, comprising preparing at least two preparations comprising adjuvanted virosomes according to claim 21 and/or using a method for preparing adjuvanted virosomes, comprising the steps of:
 (i) providing an aqueous composition of non-adjuvanted virosomes comprising a membrane fusion protein;
 (ii) dissolving an amphiphilic adjuvant in a pharmaceutically acceptable non-aqueous solvent which can form a homogeneous mixture with water; and
 (iii) diluting said adjuvant solution in said aqueous virosome composition to induce insertion of adjuvant in the outer leaflet of the virosomal membrane while preserving membrane fusion activity of the virosomes, each preparation having a distinct adjuvant/antigen ratio, and evaluating each preparation in a test subject for its efficacy in inducing an immune response.

33. The method according to claim 1, wherein the non-aqueous adjuvant solvent has a solubility in water of at least 10 g/100 mL at 20° C.

34. The method according to claim 1, wherein the non-aqueous adjuvant solvent has a solubility in water of at least 20 g/100 mL at 20° C.

35. The method according to claim 1, wherein the amphiphilic adjuvant is selected from the group consisting of α-galactosylceramide, phosphatidylinositol mannoside, and derivatives of endotoxic lipopolysaccharides.

36. The method according to claim 1, wherein said amphiphilic adjuvant is an amphiphilic peptide comprising an amino acid sequence derived from Jagged-1 or *S. aureus* protein A having adjuvant activity.

37. The method according to claim 6, wherein viral fusion protein is selected from the group consisting of the HIV gp120/gp41 proteins, the paramyxovirus F proteins and the influenza virus hemagglutinin (HA) protein, the gp64 protein of baculovirus, the E proteins of Semliki Forest virus, and fusion active variants thereof.

38. The method according to claim 8, wherein the enveloped virus is selected from the group consisting of Retroviridae; rubellavirus; paramyxoviridae; Flaviviridae; Herpesviridae; Bunyaviridae; Arenaviridae; Hantaviridae; Baculoviridae; Coronaviridae; Papovaviridae; Rhabdoviridae; Alphaviridae, Arteriviridae, Filoviridae and Poxviridae.

39. The method according to claim 9, wherein said short-chain phospholipid has a critical micelle concentration (cmc) of larger than 0.3 mM.

40. The method according to claim 9, wherein said short-chain phospholipid has a critical micelle concentration (cmc) of larger than 1 mM.

41. The method according to claim 10, wherein said phospholipid is 1,2-diheptanoyl-sn-phosphatidylcholine or 1,2-dicaproyl-sn-phosphatidylcholine.

42. The method according to claim 16, wherein the antigen is derived from influenza virus or RSV.

43. The method according to claim 18, wherein the membrane anchoring moiety is a phospholipid or acyl chain.

44. The adjuvanted virosome according to claim 22, wherein the amphiphilic adjuvant is a selected from the group consisting of mono-phosphoryl lipid A and lipopeptide.

45. The adjuvanted virosome according to claim 24, wherein the at least one of further antigen is a tumor-antigen or an antigen originating from a virus, a parasite, a fungus or a bacterium.

46. The adjuvanted virosome according to claim 24, wherein the at least one further antigen is a viral antigen derived from influenza virus or RSV.

47. The adjuvanted virosome according to claim 24, wherein the membrane anchoring moiety is a transmembrane domain, a membrane-anchoring amino acid sequence or a lipid moiety.

\* \* \* \* \*